(12) United States Patent
Brooks

(10) Patent No.: US 6,743,821 B2
(45) Date of Patent: Jun. 1, 2004

(54) GLYCEROL-LACTATE ESTERS FOR USE AS AN ENERGY SUPPLEMENT DURING EXERCISE AND RECOVERY

(76) Inventor: George A. Brooks, 1415 Richmond St., El Cerrito, CA (US) 94530

(*) Notice: Subject to any disclaimer, the term of this patent is extended or adjusted under 35 U.S.C. 154(b) by 0 days.

(21) Appl. No.: 10/158,584

(22) Filed: May 30, 2002

(65) Prior Publication Data

US 2003/0013763 A1 Jan. 16, 2003

Related U.S. Application Data

(60) Provisional application No. 60/294,516, filed on May 30, 2001.

(51) Int. Cl.$^7$ .................. A01N 37/02; A01N 37/06; A61K 31/22; A61K 31/225
(52) U.S. Cl. ..................... 514/546; 514/547
(58) Field of Search .................. 514/546, 547; 560/179, 189, 231

(56) References Cited

U.S. PATENT DOCUMENTS 6,306,828 B1 * 10/2001 Trimbo et al. ............. 514/25
6,417,231 B1 * 7/2002 Greenway et al. ......... 514/546

FOREIGN PATENT DOCUMENTS

JP 2000-60488 * 2/2000

OTHER PUBLICATIONS

Bailey et al "Calcium magnesium, and phosphorous metabolism in dogs given intravenous triacetin" Am. J. Clin. Nutr. vol. 49, pp. 385–388 (1989).*
Swensen et al "Adding Polylactate to a Glucose Polymer Solution Does Not Improve Endurance" Int. J. Sports Med. vol. 15, pp. 430–434 (1994).*

(List continued on next page.)

Primary Examiner—Mukund J. Shah
Assistant Examiner—Zachary C. Tucker
(74) Attorney, Agent, or Firm—Pillsbury Winthrop LLP

(57) ABSTRACT

A method and lactate compound for four unique purposes: (1) the provision of a fuel energy source to skeletal muscles, hearts and other tissues and organs of humans and other mammals during exercise and recovery; (2) cardiac energy supplementation following ischemia; (3) the maintenance of blood glucose and restoration of liver glycogen; and (4) the provision of fluid and electrolytes to humans and other mammals before, during and after exercise. The lactate compound is preferably a glycerol-lactate ester or a glycerol-acetate ester. Specific examples of the compound include glycerol-monolactate ester (GMLE), glycerol-dilactate ester (GDLE), and most preferably, glycerol-trilactate ester (GTLE):

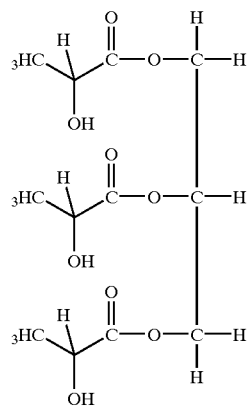

35 Claims, 5 Drawing Sheets

OTHER PUBLICATIONS

Jamie W. Lynch and James W. Bailey "Dietary Intake of the Short–Chain Triglyceride Triacetin vs. Long–Chain Triglycerides Decreases Adipocyte Diameter and Fat Deposition in Rats" Journal of Nutrition vol. 125(5), pp. 1267–1273. (1995).*

Webster's II New Riverside University Dictionary, Houghton Mifflin Co. p. 460 (1994).*

Bergman, B.C., M.A. Horning, G.A. Casazza, E.E. Wolfel, G.E. Butterfield, and G.A. Brooks. Endurance training increases gluconeogenesis during rest and exercise in men. J. Physiol. Endocrinol Metab. 278: E244–251, 2000.

Bergman, B.C., E.E. Wolfel, G.E. Butterfield, G. Lopaschuk, G.A. Casazza, M.A. Horning, and G.A. Active muscle and whole body lactate kinetics after endurance training in men. J. Appl. Physiol. 87: 1684–1696, 1999.

Burelle, Y., F. Peronnet, S. Charpentier, C. Lavoie, C. Hillaire–Marcel, and D. Massicotte. Oxidation of an oral [13C]glucose load at rest and prolonged exercise in trained and sedentary subje J Appl Physiol. 86: 52–60, 1999.

M Eyer ,C., M .S tum vo ll, J.D ostou, S .W elle, M .Haymond, and J.Gerich. R enalsubstrate exchange and gluconeogenesis in norm alpostabsorptive hum ans. Am J PhysiolEndocrinolM etab.282:E428–434, 2002.

M iller , B.F ., J.A.Fattor,K. A.Jacobs,M A.Horning,S .–H . Suh, F .Navazio, and G. A. Brooks. M etabolic and cardio respiratory responses to an exogenous lactate infusion during rest and exercise. Am. J. Physiol. Endocrinol Metab 283: E889–E898, 2002.

Miller, B.F., J.A. Fattor, K.A. Jacobs, M.A. Horning, S.–H, Suh, F. Navazio, and G.A. Brooks. Lactate–glucose interaction in men during rest and exercising using lactate clamp procedure. J. Physiol. (London) 544: 963–975, 2002.

Montner, P., D.M. Strk, M.L. Riedesel, G. Murata, R. Robergs, M. Timms, and T.W. Chick. Pre–exercise glycerol hydration improves cycling endurance time. Int. J. Sports Med. 17: 27–33, 1996.

Trimmer, J.K., G.A. Casazza, M.A. Horning, and G.A. Brooks. Autoregulation of glucose production in men with a glycerol load during rest and exercise. Am. J. Physiol. Endocrinol Metab 280: E657–E668, 2001.

Trimmer, J.K., J.–M. Schwarz, G.A. Casazza, M.A. Horning, N. Rodriguez, and G.A. Brooks. Measurement of gluconeogenesis in exercising men by mass isotopomer distribution analysis. J. Appl. Physiol. 93: 233–241, 2002.

Fahey T.D., J.D. Larsen, G.A. Brooks, W. Colvin, S. Henderson, and D. Lary. The effetcs of ingesting polylactate or glucose polymer drinks during prolonged exercise. International Journal of Sport Nutrition 1:249–256, 1991.

* cited by examiner

US 6,743,821 B2

GLYCEROL-LACTATE ESTERS FOR USE AS AN ENERGY SUPPLEMENT DURING EXERCISE AND RECOVERY

CROSS-REFERENCE TO RELATED APPLICATIONS

This application claims the benefit of U.S. Provisional Application No. 60/294,516 filed May 30, 2001 and entitled "Glycerol-Lactate Esters For Use As An Energy Supplement During Exercise And Recovery". This patent application and all other patents, patent applications, and references, are herein incorporated by reference in their entirety for all purposes, including U.S. Pat. No. 6,482,853 issued to Brooks on Nov. 19, 2002.

FIELD OF THE INVENTION

This invention relates generally to dietary energy supplements, and, in particular, to a novel method and composition beneficial to functioning of the heart, skeletal muscles and other tissues of humans and other mammals with carbohydrate energy forms during exercise stresses and subsequent recovery.

BACKGROUND OF THE INVENTION

The present invention takes advantage of discoveries of the classic (cell-cell, organ-organ) "Lactate Shuttle," and the "Intracellular Lactate Shuttle" mechanisms by Brooks (1984, 1998). The "Lactate Shuttle Hypothesis" holds that lactate plays a key role in the distribution of carbohydrate potential energy which occurs among various tissue and cellular compartments such as between: cytosol and mitochondria, muscle and blood, blood and muscle, active and inactive muscles, white and red muscles, blood and heart, arterial blood and liver, liver and other tissues such as exercising muscle, intestine and portal blood, portal blood and liver, zones of the liver, skin and blood, and astrocytes and neurons in the brain. Studies on resting and exercising humans indicate that most lactate (70–80%) is disposed of through oxidation, with much of the remainder converted to glucose and glycogen. Studies on canine muscles made to contract in situ also yield the result that lactate is rapidly oxidized (Gladden et al., Zinker et al.). Lactate transport across cellular membranes occurs by means of facilitated exchange along pH and concentration gradients (Roth and Brooks 1990a, 1990b) involving a family of lactate transport proteins now called monocarboxylate transporters (MCT's) (Garcia et al., 1994; Price et al., 1998). Current evidence is that muscle and other cell membrane lactate transporters are abundant with characteristics of high Km and Vmax. There appears to be long-term plasticity in the number of cell membrane transporters, but short-term regulation by allosteric modulation or phosphorylation is not known to occur.

The key to recognition of an "Intracellular Lactate Shuttle" is recognizing that in addition to cell membranes, mitochondria also contain monocarboxylate transporters (mitochondial MCT's or mMCT's) and lactic dehydrogenase (mLDH). Mitochondrial MCT's exist in the mitochondrial inner membrane, and possibly also the outer membrane (FIG. 1), although presence of an outer mitochondrial membrane MCT is not essential because it is highly permeable. The Intracellular Lactate Shuttle also requires presence of mitochondrial lactate dehydrogenase (mLDH) located on the inner membrane and in the intra-membrane (periplasmic) mitochondrial space. mLDH is necessary to convert lactate, the predominant plasma and intracellular monocarboxylate, to pyruvate, for transport via mMCT into the mitochondrial matrix for catalysis by pyruvate dehydrogenase (PDH) and entry into the tricarboxylic acid (TCA) cycle. Therefore, mitochondrial monocarboxylate uptake and oxidation, rather than translocation of transporters to the cell surfaces, regulate lactate flux in vivo. Key discoveries in basic science are that lactate enters mitochondria, but that pyruvate is oxidized in the mitochondrial matrix.

A. Use of Glycerol-lactate Esters for the Cardiac and Skeletal Muscle Energy

Providing energy sufficient to optimize performance is extremely important for hearts and skeletal muscles under stress of work load. Resting healthy hearts rely on exogenous, blood borne free fatty acids (FFA) as their main energy source with carbohydrate (CHO) derived fuel sources comprised of glucose and lactate playing secondary roles. For instance, in a resting person FFA may provide 80% of energy, glucose 5%, and lactate 15% (Gertz et al., 1988; Wisneski et al., 1987). However, under exercise and other stresses total energy demand increases and the fuel mix changes with the contribution of FFA falling to 40%, glucose use increasing absolutely but remaining at about 5%, and lactate the remainder (55%). During rest lactate is relegated to a minor role as an energy substrate for the heart because arterial lactate concentration is low ($\leq 1.0$ mM). However, during physical exercise lactate predominates as the cardiac fuel energy source because production in working muscle and other tissues causes blood lactate concentration to rise to a level (2–20 mM) sufficient to be taken up and oxidized within the heart. As indicated in FIG. 1, exogenous lactate gains entry to cardiocytes because of cell membrane lactate transporters. Those transporters facilitate lactate flux down concentration and hydrogen ion ($H^+$) gradients. Within cardiocytes, lactate gains entry to mitochondria via another lactate transporter pool, also along concentration and $H^+$ gradients.

Taking advantage of new knowledge of the role of lactate in cardiac and skeletal muscle metabolism, Kline et al. studied performance and efficiency of hearts removed from rabbits after hemorrhagic shock. When concentrated sodium lactate was added to the isolated working hearts taken from shocked animals, performance was significantly enhanced. This practical demonstration of the use of lactate as a fuel and anaplerotic substrate fort the TCA Cycle in hearts did not address the problem of the sodium load and its consequences imposed from either oral or intravenous administration of concentrated salt solutions.

Realizing that CHO-derived energy sources increase cardiac performance, some investigators have attempted to promote cardiac energy resuscitation after ischaemic attacks by providing glucose, sometimes with insulin and potassium. Currently used cardioplegic solutions containing glucose, insulin and potassium are sometimes referred to as GIK. Other investigators have attempted to provide pyruvate. However, from the physiological perspective such attempts are less than optimal, or misguided, because lactate, not glucose or pyruvate, is the major fuel for the heart under stress.

Recently, results of clinical trials (Ceremuzynski et al., 1999) have not confirmed viability of systemically administered GIK in the management of cardiac episodes. While GIK solutions do positively influence performance of stunned isolated hearts perfused and bathed in artificial solutions, unless GIK is administered into coronary arteries, significant effects on either cardiac performance or survival of ischaemic episodes including MI is not to be expected (Apstein and Opie, 1999). Simply, GIK can not be expected to have much effect because glucose is never the major fuel for the heart. The better approach is to provide lactate in a form that can benefit cardiac metabolism.

U.S. Pat. No. 5,294,641, herein incorporated by reference, is directed to the use of pyruvate to prevent the adverse effects of ischemia in heart muscle. The pyruvate is administered prior to a surgical procedure to increase a patient's cardiac output and heart stroke volume. The pyruvate is administered as a calcium or sodium salt. The pyruvate can alternatively be an ester of pyruvate acid such as ethylamino pyruvate. Pyruvate is used because it is a cellular energy source; but while providing exogenous pyruvate may be potentially efficacious for heart muscle, practically the applicability is limited (vide infra).

With due consideration to growing acceptance of pyruvate as an effective component of reperfusion solution, it has been recognized that traditional pharmacological pyruvate compounds, such as salts of pyruvic acid, are not particularly physiologically suitable. For example, inorganic salts of pyruvate lead to the accumulation of large concentrations of inorganic ions (e.g., potassium, calcium or sodium) in body fluids. Accordingly, while potentially suitable to organ preservation, the salt-pyruvate compounds are not ideally suited to treating an organ or supplementing energy in an active person in vivo, and it is recognized that a need exists to deliver a monocarboxylate (pyruvate-like) compound with is more physiologically appropriate.

In this regard, U.S. Pat. No. 5,283,260, herein incorporated by reference, is directed to treatment of diabetes with a physiologically acceptable form of pyruvate. The patent discloses a pyruvate compound in the form of a covalently linked pyruvate-amino acid. By utilizing this type of pyruvate delivery system, the negative effects of inorganic-pyruvate salts are avoided. However, administration of large amounts of pyruvate-amino acid compounds may result in an amino acid nitrogen overload which could harm patients with liver and/or kidney pathology.

Similarly, U.S. Pat. No. 5,667,962, herein incorporated by reference, is directed to use of pyruvate thiolester for the prevention of cardiac reperfusion injury. The intention of that invention is to provide a compound comprising covalently linked pyruvate and N-acetylcysteine. However, the design of the material is flawed in its purpose and mode of action.

Not withstanding use of compounds of complexes of pyruvate and pyruvate-compounds in cardioplegia and organ transplantation procedures, as well as covalently linked compounds involving mixtures of pyruvate and amino acids with antioxidant characteristics such as embodied in the above-identified U.S. patents, the emphasis on pyruvate as a monocarboxylate to deliver to stressed organs and tissues is misplaced. In fact, any attempts to utilize pyruvate as an agent to improve the status of working heart and skeletal muscles results in a delayed response because lactate, not pyruvate, is the preferred compound exchanged ("shuttled") among organs, tissues, cells, and intracellular compartments. Tissue levels of lactate exceed those of pyruvate by 10 to 100-fold, and cell membrane monocarboxylate transporters are specific to lactate, not pyruvate. Beneficial effects of pyruvate administration accrue only after conversion to lactate, which is the preferred material for cell-cell exchange via the "Lactate Shuttle."

As stated by Sumegi et al. (p. 77) who utilized nuclear magnetic resonance spectroscopy (NMR) and [3-$^{13}$C] pyruvate tracer to study pyruvate metabolism in hearts of living rats: "The infused [3-$^{13}$C]pyruvate was quickly converted to [3-$^{13}$C]lactate in the blood of Wistar rats." [NB, this pyruvate to lactate conversion is due to presence of lactate dehydrogenase (LDH), an enzyme highly abundant in erythrocytes, such that in blood the lactate/pyruvate ratio is normally 10 and can increase an order of magnitude under physiological stress (Brooks, 1998).] Surprised by their results and unable to explain them, with some trepidation Sumegi et al. went on to state (p. 80): "These data show that the extracellular lactate is preferentially taken up by a portion of cytoplasm which converts lactate to pyruvate and transfers it to the mitochondrial reticular network." However, in making the statement concerning conversion of lactate to pyruvate in cytoplasm, Sumegi et al. recognized a major problem in interpretation of their data. By failing to recognize the existence of a mitochondrial form of lactic dehydrogenase (mLDH, FIG. 1), they had to "assume that a fraction of the cytoplasm associated with the mitochondrial reticular network is specialized for converting the lactate to pyruvate, with the pyruvate being channeled to the mitochondria." [NB, in striated muscle (i.e., heart and skeletal) mitochondria do not exist as discrete organelles, but as part of a large, interconnected network, the Mitochondrial Reticulum (Kirkwood, et al.)]. As indicated by presence of mLDH (FIG. 2), the highly improbable assumption of Sumegi et al. is unnecessary, and the same physiological result is readily accomplished because of LDH.

Paradoxically, the addition of exogenous lactate to the blood of mammals has alkalinizing effects because lactate removal from the blood, whether by oxidation or gluconeogenesis, requires a proton (in the ratio of 1:1, protion:lactate anion) for transport and metabolism. Thus, by virtue of the acid/base chemistry in mammals, addition of lactate anion to plasma mitigates the presence of lactic acidosis.

(1) Data of Cell Membrane Lactate Uptake Taken from Roth and Brooks (1990a, 1990b)

Sarcolemmal vesicles were isolated from rat skeletal muscle and effects of various monocarboxylates including L(+) and D(-) lactate (FIG. 2), and other monocarboxylates were determined (Roth and Brooks, 1990a, 1990b). Results indicate saturation kinetics and stereospecificity for the L(+) compared to the D(-) isomer of lactate.

These and other characteristics (e.g., pH dependency, temperature sensitivity and inhibition by known monocarboxylate inhibitors such as CINN, vide infra) indicate presence of a sarcolemmal lactate transport protein. Further, results indicate far greater affinity for lactate (FIG. 2), than for pyruvate (FIG. 3).

(2) Data of Mitochondrial Lactate Uptake and Oxidation Taken from Brooks et al., 1990a (a) Inhibition of Mitochondrial Lactate and Pyruvate Uptake and Oxidation by CINN: Traditionally, several substrates, and combinations of substrates have been used to study mitochondrial respiration in vitro. Pyruvate-malate has usually been used to probe mitochondrial Complex I, succinate Complex II, and TMPD+ascorbate Complex III. In contrast, lactate or lactate-malate has been infrequently used. However, pyruvate and lactate are known to share the sarcolemmal lactate transporter(s), and pyruvate gains access to the mitochondrial matrix by means of facilitated transport. Oxidation of lactate by isolated mitochondria is permitted by the presence of a mitochondrial pool of LDH which provides matrix pyruvate from exogenous lactate. To establish that lactate gains access to the mitochondrial matrix via facilitated exchange via a monocarboxylate (ACT) transport protein, we utilized polarography and inhibition by the known MCT inhibitor α-cyano-4-hydroxycinnamate (CINN). Results on rat liver mitochondria are shown in FIG. 4.

Results show CINN inhibition of pyruvate and lactate oxidation, but bypass of the CINN block by succinate, which gains access to the matrix by a different transport mechanism and which donates electrons to Complex II, in contrast to lactate and pyruvate which are NADH-linked substrates and donate electrons to Complex I. Additionally, results of experiments on rat liver mitochondria with 10 mM glutamate as substrate show no measurable effect of CINN on states 3 or 4 respiratory rate, RCR and ADP/O (data not shown). Absence of an effect of CINN on glutamate oxidation by isolated mitochondria is of value because, like pyruvate, glutamate is an NADH-linked substrate. Thus, the effect of CINN on pyruvate and lactate oxidation is upstream of Complex I.

(b): Presence of MCT1 or a MCT1 Homologue in Mitochondria: Mitochondria were isolated from skeletal muscle, rat liver and heart by standard techniques of cell fractionation. Subsequently, skeletal muscle mitochondria were probed with a polyclonal antibody to the C-terminus of rat MCT1 (N'-CPLQNSSGDPAEEESPV-C'), and results of a Western blot analysis displayed in FIG. 5. The results indicate presence of a mitochondrial protein which reacts with an antibody to the C-terminus of MCT1. To exclude the possibility of contamination from sarcolemmal MCT1 in the mitochondrial preparation, mitochondrial and cell membrane fractions were probed with antibodies to MCT1 and the cell membrane Glucose Transport Protein #1 (GLUT1). Scarcely detectable levels of GLUT1 in mitochondrial indicate minimal contamination from cell membranes in the mitochondrial preparation. Thus, it is evident that rat striated muscle mitochondria contain a monocarboxylate transporter with high homology to MCT1. Further, similar results have been obtained on human skeletal muscle and muscle mitochondria (Dubouchaud et al.).

(c): Presence of Lactic Mitochondrial Dehydrogenase (mLDH): Mitochondria were isolated from rat liver and heart by standard techniques of cell fractionation. Subsequently, mitochondria were treated by gel electrophoresis and the results displayed in FIG. 6. The results indicate presence of mitochondrial LDH, which is mainly of the H4 isoenzyme in heart and red skeletal muscle (not shown). In contrast, liver mitochondria contain only the LDH5 isoform, whereas both LDH4 and LDH5 are present in cytosol of rat liver. These results support the conclusion of separate cytosolic and mitochondrial pools of LDH in rat muscle, liver and heart. Again, the presence of LDH in human muscle mitochondria has been demonstrated (Dubouchaud et al.).

Accordingly, it is desirable to have an alternative physiologically compatible therapeutic compound based on lactate, not pyruvate for lactate is the monocarboxylate selected by nature for exchange in the blood and between and among cells, tissues, organs and intracellular compartments. Again, pyruvate added to the circulation will need to be converted to lactate prior to entry into cells. The sites of this conversion will be erythrocytes or cytosol of cardiac and skeletal muscle cells. Therefore, provision of pyruvate will only slow delivery of monocarboxylate material for mitochondrial oxidation.

B. Use of Glycerol-lactate Esters as an Energy Source Supplement During Exercise and Recovery:

Recent advances in basic biochemistry and exercise physiology have shown that the formation and removal of lactic acid is an integral part of both digestive and metabolic processes. Further, as lactate is a fuel for the heart (vide supra), it is also a major energy source in working skeletal muscle.

According to the 'Glucose Paradox' hypothesis (reviewed by Foster, 1984; see also Newgard et al., 1983), dietary carbohydrate courses an indirect route before becoming liver glycogen. It is known that dietary carbohydrate is digested and than enters the portal circulation (i.e., that vein between the small intestine and the liver) largely as glucose.

In contrast to traditional theories which hold that the liver extracts large amounts of portal blood glucose for synthesis of glycogen, it is now believed that portal glucose bypasses the liver and enters the systemic circulation through the hepatic vein. Much of this glucose then reaches the resting musculature, where it is either stored as glycogen or converted into lactic acid. This lactic acid then either diffuses or is transported from the sites of production and reaches the systemic circulation. Much of the circulating lactic acid is removed by the liver.

In the glycogen-depleted liver, lactic-acid becomes the preferred precursor material from which to synthesize glycogen. Because glycogen is paradoxically synthesized by a rather circuitous pathway, the process is alternatively termed the Glucose Paradox, or the Indirect Glucose to Liver Glycogen Pathway.

According to the 'Lactate Shuttle" hypothesis (Brooks, 1985, 1986a, 1986b), 1987, 1998, 1999a, 1999b); lactic acid is an important fuel source for exercise as well as resting and exercise-recovery conditions (FIG. 7). During exercise, active fast-twitch muscles produce lactic acid, which is then available as a fuel for slow-twitch, highly oxidative skeletal muscle fibers (Donovan and Brooks, 1983). This process appears to operate all the time as demonstrated in human subjects exercising at sea level (Bergman et al 1999; Mazzeo et al. 1986; Stanley et al. 1985, 1986, 1988), or high altitude (Brooks et al., 1991, 1992). In fact, based on conclusions conducted on rats (Brooks and Donovan, 1983; Donovan and Brooks, 1983) and humans (Bergman et al., 1999; Brooks, 1992; Stanley et al., 1988), lactate appears to be a more important fuel for muscular exercise than does glucose, especially during sustained exercise and recovery form sustained, exhausting exercise (FIG. 8).

Results of studies conducted by Gladden and associates (1991, 1994) on canine muscles made to contract in situ support observations made on human subjects. The data clearly show that working canine muscles consume and utilize lactate in a concentration-dependent manner.

The oxidation of lactic acid during exercise can be appreciated on both relative and absolute bases. Of the lactic acid produced and removed during exercise, approximately 75% is removed by oxidation and about 20% is converted to glucose (Bergman et al. 1999; Donovan, C. M. and G. A. Brooks, 1983; Stanley et al., 1988, Brooks et al, 1991b, 1992). Of this latter portion, most will ultimately be oxidized also (Brooks, and Donovan, 1983, Brooks et al. 1992). Quantitatively, lactic acid oxidation exceeds glucose oxidation during exercise with 10–25% of the total energy supplied derived from lactic acid oxidation. These findings suggest that it may be desirable to employ lactic acid as a supplement during and/or after exercise.

However, the use of lactic acid as a fuel in the body carries with it potential penalties. Lactic acid accumulation in the muscle is painful and interferes with contraction processes. Further, large amounts of lactic acid in the blood cause pH to fall which is physically and psychologically distressing to the performer. These disadvantages are associated with the hydrogen ion ($H^+$, or proton) which results when lactic acid dissociates in aqueous solutions. For these reasons lactic acid accumulation has long been suspected as a cause of muscle fatigue (Brooks et al., *Exercise Physiology: Human*

*Bioenergetics and its Applications,* Chapter 33, Mayfield, Mountainview, Third Edition, 2000).

Therefore, it may be advantageous to provide a carbohydrate derived fuel source to an individual engaged in prolonged, strenuous exercise, and it would be more efficacious to provide the carbohydrate energy in the form of a 'lactic acid-like' substance which would provide a more immediate fuel source.

Thus, on the bases of both the 'Glucose Paradox" and 'Lactate Shuttle' concepts, providing a 'lactic acid-like' material to athletes during exercise and recovery from exercise would also augment the beneficial effects of providing dietary glucose.

SUMMARY OF THE INVENTION

This invention relates to a new lactate compound and a method of: (1) providing energy to the heart and skeletal muscles during physical exercise and recovery from exercise, and (2) providing a supplemental energy source to active mammals during exercise and recovery from exercise. The invention is particularly directed to: (1) a method of cardiac and skeletal muscle energy supplementation during and following energy demanding activities, (2) a method of replenishing energy in active individuals, (3) a method of maintaining blood sugar (glucose) in exercising individuals and restoring liver carbohydrate stores (glycogen) during recovery from exercise, and (4) a method of hydrating and rehydrating individuals during exercise and recovery. The inventive method is constructed to benefit: (1) cardiac and skeletal muscle energy resuscitation during and following strenuous exercise, and (2) increase the energy supply and vigor of active individuals. Accordingly, the global objective of this invention is to provide a new and improved lactate compound.

Specific objectives of this invention are, in mammals:

(1) to provide a new and improved method to provide energy to the stressed heart, (2) to provide a new and improved method to provide energy to stressed skeletal muscle, and (3) to provide a new and improved method to supply supplemental energy to exercising individuals, and (4) to facilitate hydration of individuals before, during and after exercise.

To achieve the foregoing objects and in accordance with the purpose of the invention, as embodied and broadly described herein, the novel lactate compound of this invention comprise a glycerol-lactate ester (GLE). Preferably, the ester is in the tri-lactate form, but other lactate-ester forms (di- or mono-lactate esters), as well as glycerol-acetate esters (GAE) will serve similar functions. In a particularly preferred form, the compound is a tri-lacteal ester of the glycerol.

Each objective of the invention can be accomplished in mammals, including, but not limited to, horses, canines, and humans. In a most preferable embodiment, this invention envisions treating humans.

The general form of the compound is:

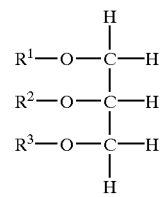

where $R^1$, $R^2$, and $R^3$ are selected from lactoyl or acetyl groups.

In a the most preferable embodiment, the composition has the formula:

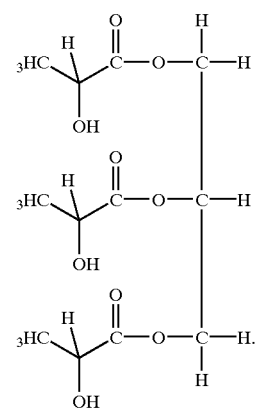

The invention is directed to use of the novel lactate compound for intravenous, intracoronary, or oral introduction, most preferably oral. Accordingly, the invention includes methods for providing fluid, energy and electrolytes to physically active persons or those exposed to hot, and hot-humid environments, as well as for the preservation of tissue deprived to oxygen through events including, but not limited to, coronary infarction, stroke, mesenteric infarction, organ transplant (during preservation and intravenously after grafting to the organ), including amputated limbs. The composition can be used on any organ or tissue in the body, including, but not limited to, cardiac muscle, skeletal muscle, or brain.

In accordance with the present invention, in addition to providing an energy source following prolonged and demanding exercise, GLE is presented as a novel method and composition beneficial to a mammal's fluid, electrolyte and carbohydrate balance during exercise and subsequent recovery are provided.

In one aspect, the invention provides a method of supplying nutritional supplementation to humans and other mammals by means of an aqueous solution of at least one lactic acid salt. This solution is administered in oral dosage form to the host in an amount sufficient to affect the mammal's fluid, electrolyte or carbohydrate balance during exercise and/or subsequent recovery.

In another aspect, a nutritional supplement is provided comprising an aqueous solution of at least one lactic acid salt in an amount sufficient to affect a mammal's fluid, electrolyte or carbohydrate balance during exercise and/or subsequent recovery.

In another aspect a nutritional supplement is provided to maintain blood glucose during exercise and restore liver glycogen after exercise.

In other aspects, the present nutritional supplement includes mixtures of organic and inorganic lactic acid salts, lactate polymers, and/or simple complex carbohydrates. Such mixtures containing fructose, glucose polymers and larger polysaccharides for provision of fuel energy via enteral (oral) administration represent a different adaptation of the composition than for cardioplegic administration into the blood.

BRIEF DESCRIPTION OF THE DRAWINGS

FIG. 2: L(+) and D(−) lactate transport kinetics in rat sarcolemmal vesicles at various concentrations of isomers. Data are mean±SEM. Lineweaver-Burk plot of the L(+) lactate data. From Roth and Brooks, 1990a.

FIG. 4: Reproduction of a Clark $O_2$ electrode tracing indicating inhibition of mitochondrial oxygen consumption in rat liver mitochondria with lactate or pyruvate as substrates in presence of CINN. Respiration is not affected with succinate as substrate. From Brooks et al., 1999a.

FIG. 6: Agarose gel electrophoresis of LDH in mitochondria from rat liver and heart. LDH isoenzyme patterns differ between cytosol and mitochondria in both tissues. From Brooks et al., 1999a.

DETAILED DESCRIPTION OF THE PREFERRED EMBODIMENTS

Figure 1:
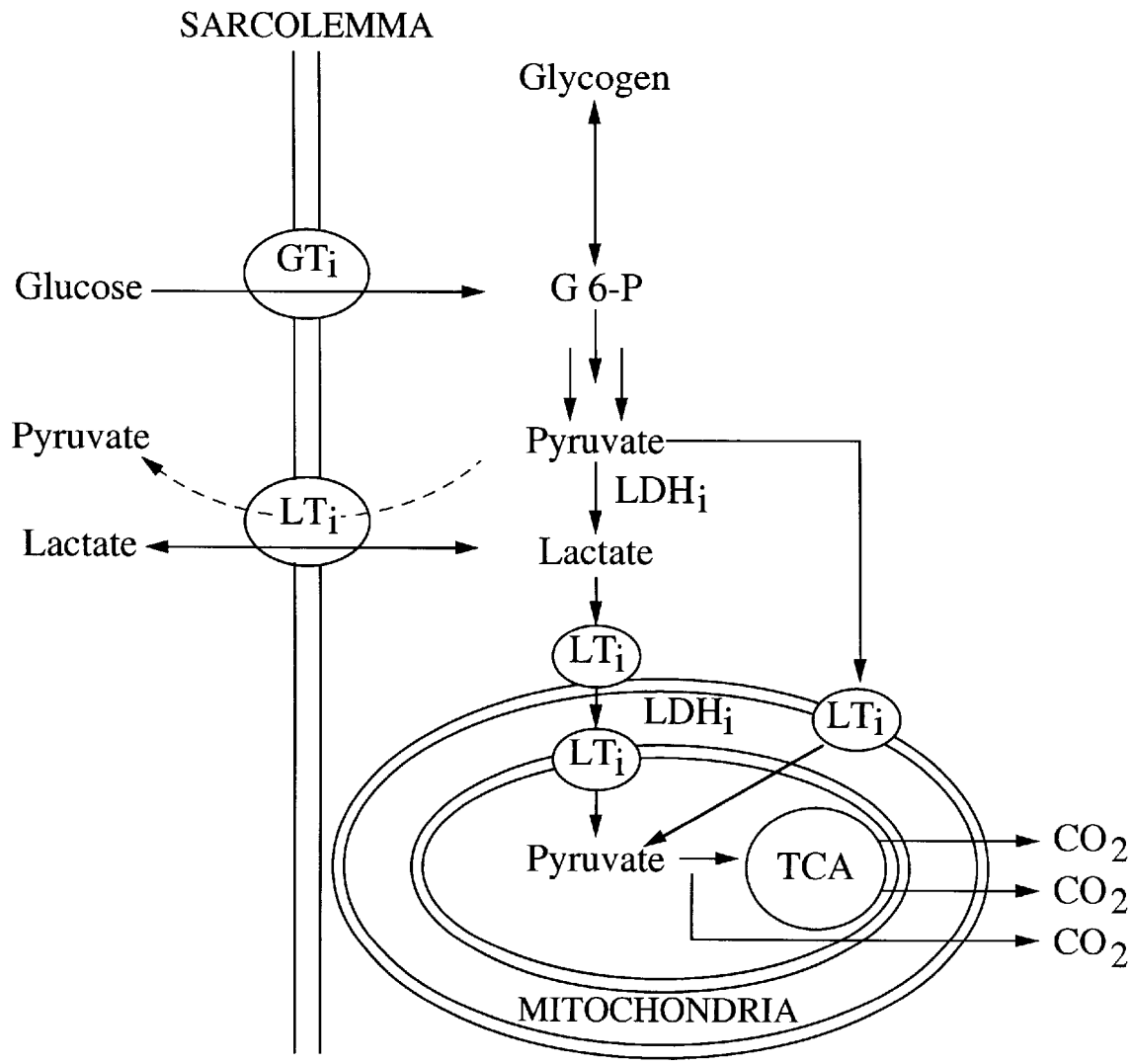
FIG. 1: Model of an "Intracellular Lactate Shuttle showing the central role of lactate in coordinating lactate among and between cells. The model presupposes presence of a family of isoforms of lactate transport proteins ($LT_i$) which likely possess tissue specificity. Additionally, the model presupposes existence of mitochondrial LDH (mLDH), and lactate (monocarboxylate) transporter, or mMCT isoforms. From Brooks (1998, 1999).
Figure 2:
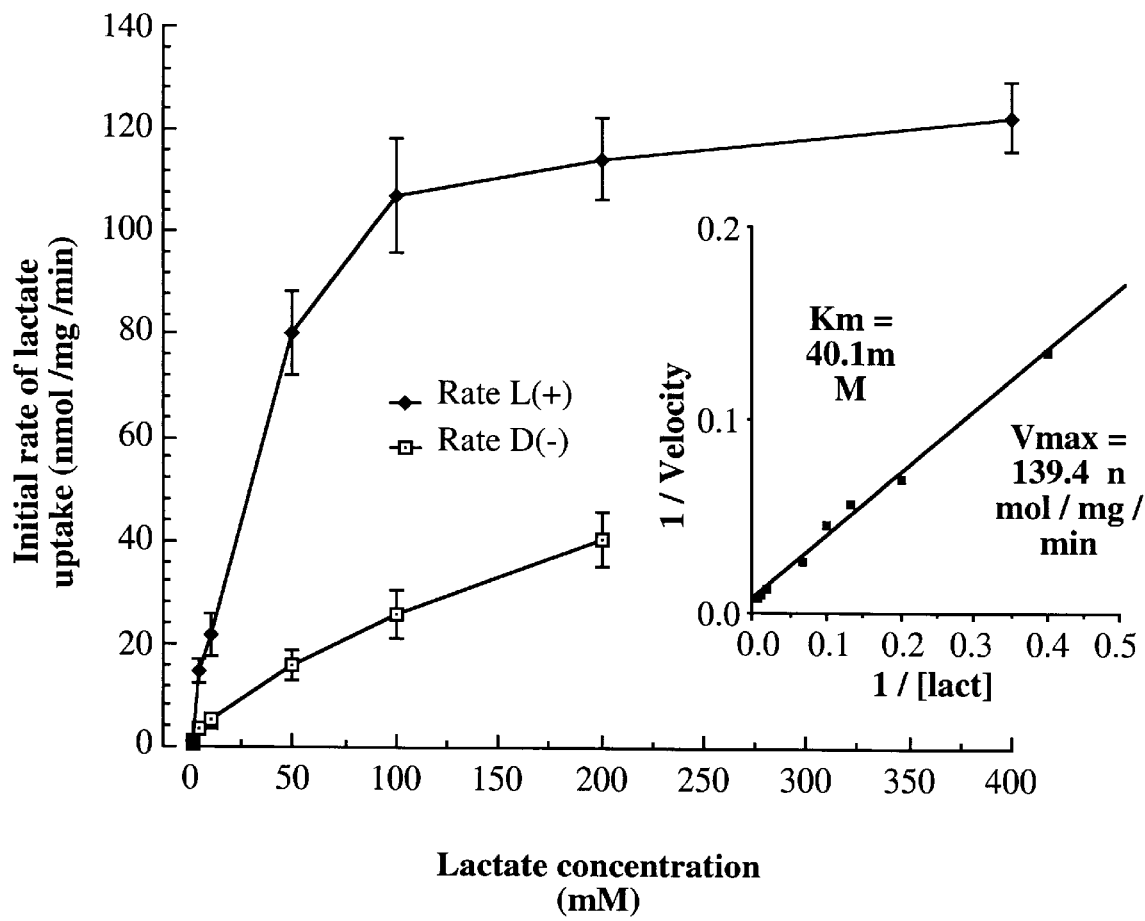
Figure 3:
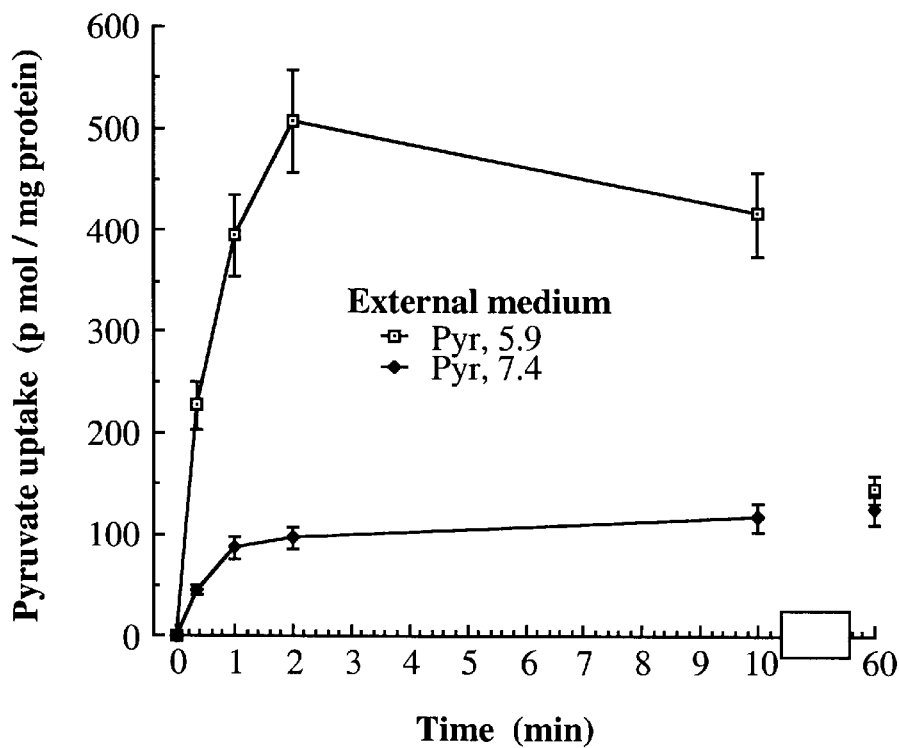
FIG. 3: L(+) pyruvate transport kinetics in rat sarcolemmal vesicles over time. Data are mean±SEM. Lineweaver-Burk plot of the L(+) lactate data. From Roth and Brooks, 1990b. Results show pH dependency for pyruvate transport, but values are far less than for lactate transport illustrated in FIG. 2.
Figure 4:
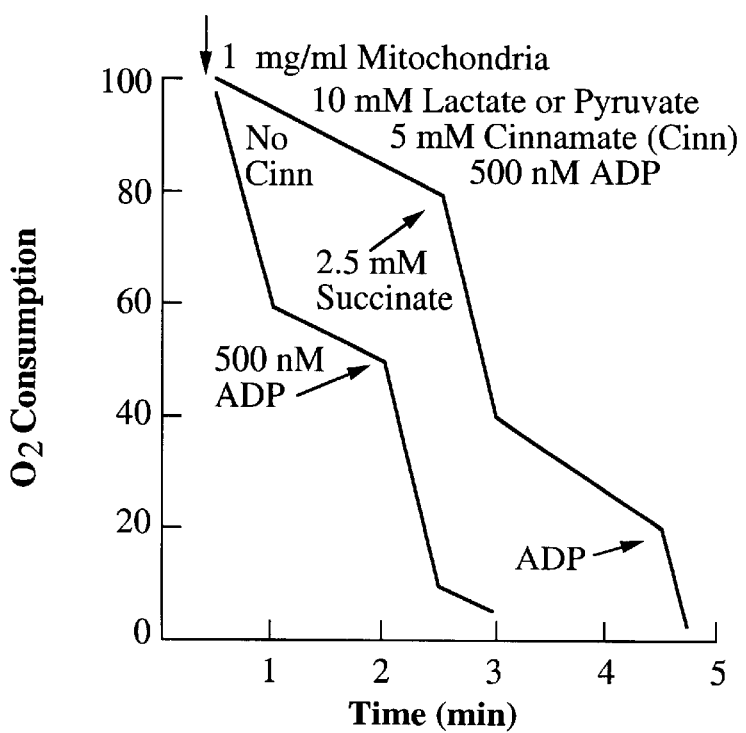
Figure 5:
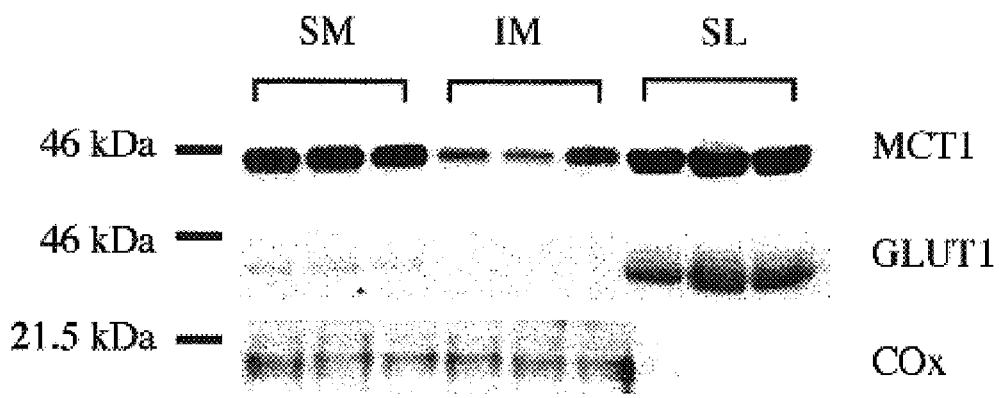
FIG. 5: Western blot showing responses of different rat cardiac muscle mitochondrial and cellular fractions probed with antibodies to MCT1, GLUT1 and cytochrome oxidase. The antibody to MCT1 responded strongly to subsarcolemmal (SM) and interfibrillar (IM) mitochondria and sarcolemmal (SL) membranes. Mitochondrial fractions reacted to cytochrome oxidase, but not to GLUT1; cell membranes did not react to cytochrome oxidase. From Brooks et al., 1999b.
Figure 6:
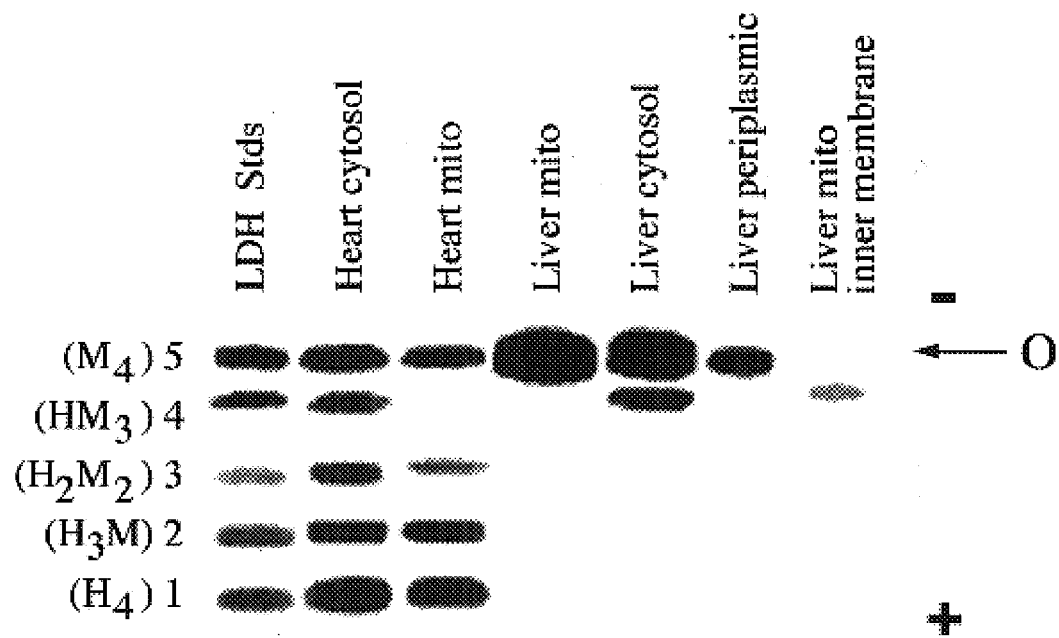
Figure 7:
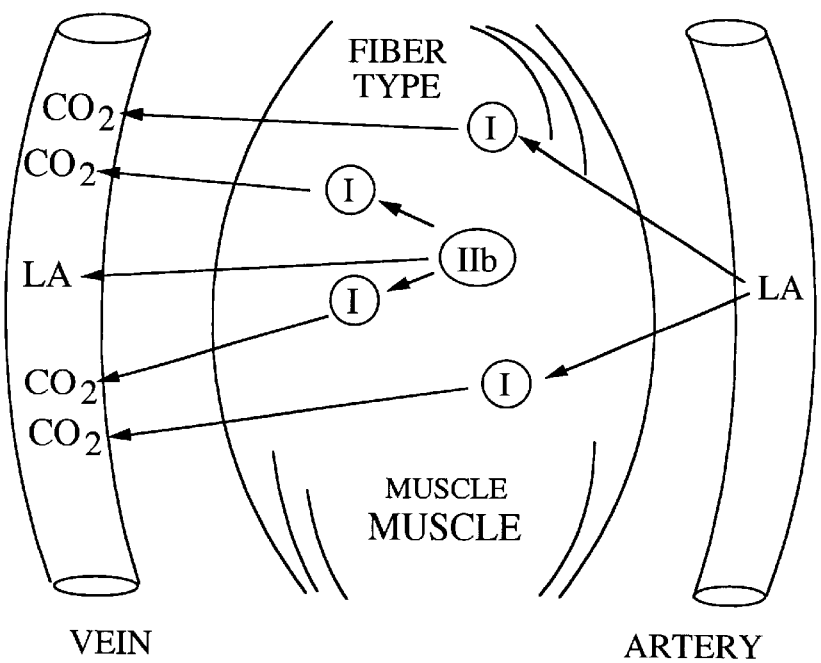
FIG. 7: A diagrammatic representation of the biochemical pathways known as the 'Lactate Shuttle', by which lactate formed in some tissues, such as contracting white skeletal muscle fibers (FG, fast glycolytic, Type IIb) fibers, provides an energy source for other tissues such as contracting red skeletal muscle (SO, slow oxidative, Type I) fibers and heart. From Brooks, 1984.
Figure 8:
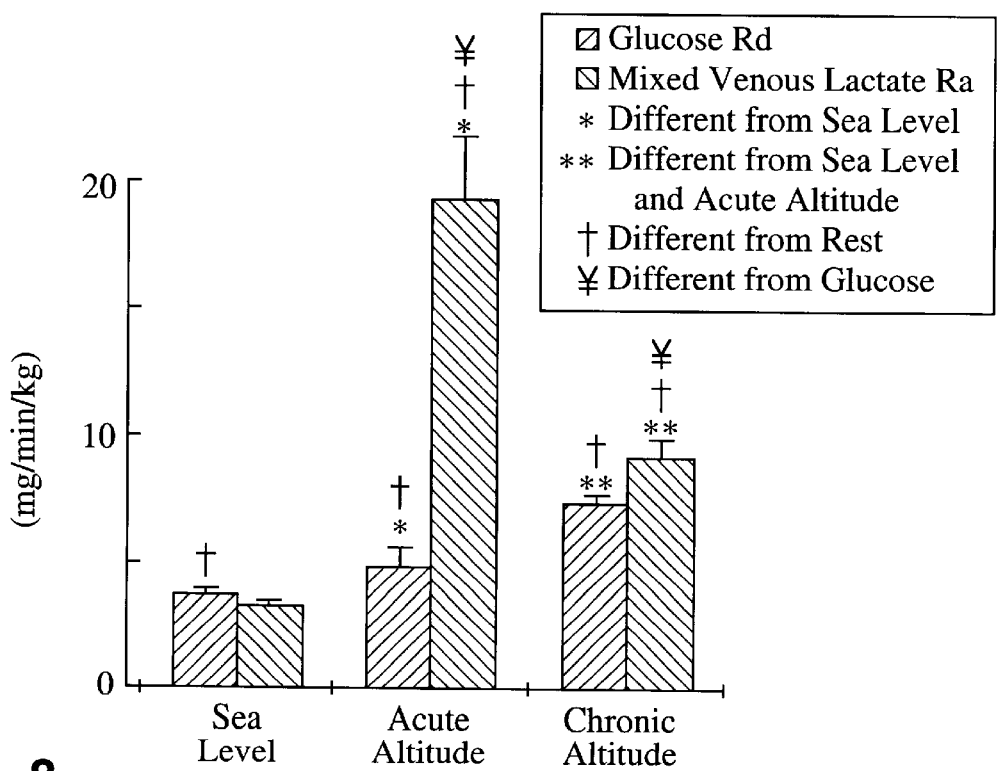
FIG. 8: Effects of altitude exposure and acclimatization on blood glucose disappearance (Rd) and lactate appearance (Ra). Resting values (panel A) are contrasted with those determined during exercise (panel B); (n=6 or 7). Statistical differences as indicated on the figure. From Brooks et al, 1991B.

As described above, timely provision of energy, fluid and electrolytes to exercising mammals or those suffering from exercise-induced or other forms of dehydration (e.g., diarrhea) is essential. Moreover, timely provision of energy to the heart will facilitate treatment for acute myocardial infarction (MI) by improving cardiac performance, thereby reducing myocardial infarct size and improving survival rates from MIs. However, there is concern that reperfusion may cause further injury to the myocardium, called "reperfusion injury."

The present invention anticipates and avoids the occurrence of reperfusion injury when used to treat any mammal, more preferably horses, canines, and humans, most preferably humans. The invention can be used to treat any tissue or organ, including, but not limited to, cardiac tissue, skeletal tissue, and brain. The treatment may be introduced intraveinously, intracoranously, or orally, with or without additional components.

In a preferred embodiment, a compound which includes a lactate moiety that provides energy for mitochondrial oxidation, as well as promotes intestinal absorption of energy, fluid and electrolytes, is used. The disclosed compounds and family of compounds provide dual functionality in an effective and highly efficient manner and in a physiologically soluble way. In addition, the compounds are degraded to physiological and safe metabolites (e.g., lactate and acetate anions, and glycerol).

The inventive compounds demonstrate the following characteristics:

(i) water solubility;
(ii) no ionic charge to interfere with diffusion through cell membranes, but could be administered in combination with counter-ions such as $Na^+$, $K^+$, $Mg^{++}$, $Ca^{++}$, or $NH_4+$;
(iii) metabolizable to physiological compounds in the stomach and GI tract; and
(iv) stability in solution ex vivo.

The compounds are preferably glycerol esters of lactate or acetate (e.g., glycerol-mono-, di- and tri-lactates; and glycerol-mono-, di- and tri-acetates. The most preferred compound is formed of lactic acid and glycerol.

Glycerol acts primarily as a non-acidic lactate carrier molecule that has the advantage of being an effective means to maintain and expand plasma volume (Miller et al., 1983). It is a naturally occurring body substrate that appears in the body as the result of dietary absorption or as the product of triglyceride lipolysis (fat breakdown). Glycerol is metabolized mainly in the liver where it serves as a gluconeogenic precursor, and is metabolized to a lesser extent peripherally (Trimmer et al.). As the result of rather slow clearance from plasma, the presence of glycerol in plasma serves to hold water in that plasma compartment. Thus, oral glycerol has been used to increase plasma volume. Therefore, glycerol made available from hydrolysis of glycerol-lactate esters in the stomach and upper GI tract will provide a secondary function, that of facilitating hydration of those anticipating being active in warm environments as well as rehydrating persons after exercise-induced or other forms of dehydration. In addition, a tertiary role of glycerol will be its availability as a gluconeogenic precursor. Though relatively poor in this regard compared to lactate, enteral glycerol will have a first-pass effect on the liver and with lactate, benefit the processes of hepatic gluconeogenesis (making new glucose) and glyconeogenesis (making new liver glycogen).

One embodiment of the invention is a solution of esters of lactic acid and glycerol. For example, the solution may comprise about 1–10% w/v of a mixture consisting of about 10–20% an inorganic salt of lactic acid and about 80–90% GLE (or GAE). In this example, the inorganic lactic acid salt can be selected from the group consisting of sodium lactate, potassium lactate, magnesium lactate, calcium lactate, and ammonium lactate. The aqueous solution can additionally comprise simple and/or more complex carbohydrates. The simple carbohydrates can include glucose or fructose. More complex carbohydrates appropriate for the solution include carbohydrates selected from the group consisting of glucose polymers from five to ten monomeric units. An effective amount of the solution may be administered to humans or other mammals orally, intravenously, or intracoronarily to provide to the humans or other mammals fluid, energy (e.g., carbohydrates) and electrolytes. The solution may also be used for the preservation of oxygen-deprived tissues.

For example, for oral rehydration, the supplement described above may include, as a simple carbohydrate, approximately 2–4% glucose in order to provide ready support of blood glucose level. In this way, metabolism in glucose-dependent cells is supported as is muscle glycogen restitution during recovery. Alternatively, fructose can be used as a supplement to or replacement for glucose to provide similar benefits in the supplement. This glucose-enhanced supplement can also be used for cardioplegic application.

For oral administration, the supplement will desirably contain at least one complex carbohydrate, such as a glucose polymer, to provide carbohydrate energy in a form to minimize osmotic pressure, thereby maximizing gastric emptying and intestinal absorption. In certain embodiments, the percent glucose polymer to provide the desired carbohydrate energy source may be increased to 4%. For example, of the other simple sugars and multi-dextrans supplied as an adjunct to GLE, the mixture might contain 1% glucose, 1% fructose, and 2% multi-dextran, or any combination so that the total simple sugar-multi-dextran adjunct to GLE is in the range of 2–4%.

In addition, a side benefit of supplying energy in the form of a lactate-containing compound is the ability to provide minor amounts of inorganic lactate salts in solution (e.g., sodium, potassium, magnesium, and calcium). In contrast to sarcolemmal transport which is hydrogen ion ($H^+$)-mediated, intestinal lactate (and glucose) is sodium ($Na^+$)-mediated. Thus, inclusion of 0.2% $Na^+$-lactate with 2% GLE, and 2–4% other simple sugars and multi-dextrans, would yield a solution that readily promotes fluid, electrolyte, and energy balance and restoration in athletes and other active persons. Similarly, such a beverage would represent an ideal means to treat diarrhea in infants and others.

It must be realized at this point that, with possible exception of the sodium lactate component which should not be increased beyond the stated ranges, it is possible to adjust the proportions of the above stated components of the present supplement across a broad concentration range.

For example, it is possible to substitute calcium, potassium, ammonium and/or magnesium lactate for sodium lactate. The preferred substitutions will be for minor amounts of sodium ion as follows:

5 $mEq(K^+)$, 2 $mEq(Ca^{++})$, 1 $mEq(Mg^{++})$, and <1 $mEq(NH_4^+)$.

For cardioplegic application, the supplement preferably includes 5 mEq ($K^+$).

Specific examples of the GLE include glycerol-monolactate ester (GMLE), glycerol-dilactate ester (GDLE), and most preferably, glycerol-trilactate ester (GTLE):

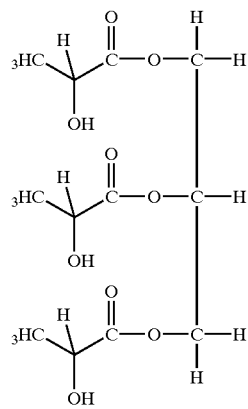

Furthermore, the invention involves use of mixtures of lactate- and pyruvate compounds as well as hexoses (glucose and fructose), maltodextrins and electrolytes as adjutants to support GLE in its specific purposes.

The invention will now be described with reference to the following examples, intended to describe, but not limit the invention to any particular form of synthesis or manufacture.
Synthesis of GLE Lipase enzymes have been successfully used as catalysts for esterification of molecules that contain at lease one hydroxy or acid group (Kirchner et al.). To date, attention has been on application of lipase-enzyme synthesis of medium to long chain fatty alcohols for the purpose of producing compounds of cosmetic value and treating particular skin diseases (Torres and Otero). However, the short chain polyalcohol glycerol contains three carbons and three hydroxyl groups and, therefore, is an appropriate structure for esterification of lactic acid and glycerol.

Synthesis in Organic Solvents: The enzymes used can be *Candida rugosa* lipase, Pseudomonas sp. lipase, *Mucor miehei* lipase, and Lipase B from *Candida antarctica*. Of these Lipase B from *Candida antarctica* is preferred and can be obtained under the trade name of Novozym 435 from Novo Nordisk A/S (Bagsvaerd, Denmark). In a glass stopped bottle, 50 mg (0.55 mmol) of L-lactic acid, 51 mg glycerol (0.55 mmol), 2 ml organic solvent (acetone or acetonitrile) are mixed. The enzyme (25 mg, or $5.7 \times 10^{-6}$ $\mu$/mg activity) is added and the mixture gently shaken for 24 hr at 50° C. ester yield should approximate 50%. After completion, the enzyme and solvent can be eliminated by filtration and evaporation, respectively. The ester can be separated from reactants by liquid chromatography.

Synthesis in Aqueous media: Toxicity of the product due to contamination by organic solvents can be avoided by eliminating use of organic solvents. The use of organic solvents facilitates esterification of lactic acid to long chain alcohols, but glycerol and lactic acid are readily miscible with the water contained in commercial lactic acid preparations providing the necessary solvent phase. As well, esterification can be facilitated by raising the lactic acid/glycerol ratio to 3/1, and increasing the reaction temperature to 60° C. Moreover, ethyl lactate can be used as an alternative to lactic acid. In a glass stopped bottle, 150 mg (1.65 mmol) of L-lactic acid, 51 mg glycerol (0.55 mmol) are mixed. Fifty mg of Novozym 435 lipase are added and the mixture gently shaken for 48–72 hr at 60° C. ester yield should approximate 70%. After completion, the enzyme and solvent can be eliminated by filtration, and the ester can be separated from reactants by liquid chromatography not withstanding that the reactants (lactate and glycerol) are benign.

U.S. Patent Documents Cited
5,283,260 February 1994 Miller et al. . . . 514/563
5,294,641 March 1994 Stanko . . . 514/540
5,420,107 May 1995 Brooks
5,667,962 September 1997 Brunengraber et al.
Other Publications Cited Allen, P. J., and G. A. Brooks. Partial purification and reconstitution of the sarcolemmal L-lactate carrier from rat sketetal muscle. Biochem. J. 303:207–212, 1994.

Apstein, C.S., and L. H. Opie. Glucose-insulin-potassium (GIK) for acute myocardial infarction: a negative study with a postive value. Cardiovasc. Drugs Ther. 13: 185–189, 1999.

Bergman, B. C., E. E. Wolfel, G. E. Butterfield, G. D. Lopaschuk, G. A. Casazza. M. A. Horning, and G. A. Brooks. Active muscle and whole body lactate kinetics after endurance training in men. J. Appl. Physiol. 87: 1684–1696, 1999.

Brooks, G. A. Lactate: Glycolytic end product and oxidative substrate during sustained exercise in mammals—the "lactate shuttle." In, Comparative Phyiology and Biochemistry—Current Topics and Trends, Volume A, Respiration—Metabolism— Cirulation, R. Gilles (Ed.), Berlin, Springer-Verlag, 1984, pp. 208–218.

Brooks, G. A. Lactate production under fully aerobic conditions: The Lactate Shuttle during rest and exercise. Federation Proc. 45:2924–2929, 1986.

Brooks, G. A. Current concepts in lactate exchange. Med. Sci. Sports Exerc. 23:895–906, 1991.

Brooks, G. A. Mammalian Fuel Utilization During Sustained Exercise. Comp. Biochem. Physiol. 120: 89–107, 1998.

Brooks, G. S., M. A. Brown, C. E. Butz, J. P. Sicurello, and H. Dubouchaud, Cardiac and skeletal muscle mitochondria have a monocarboxylate transporter MCT1. J. Appl. Physiol. 87: 1713–1718, 1999.

Brooks, G. A., G. E. Butterfield, R. R. Wolfe, B. M. Groves, R. S. Mazzeo, J. R. Sutton, E. E. Wolfel and J. T. Reeves. Increased dependence on blood glucose after acclimatization to 4,300 m. J. Appl. Physiol. 70:919–927, 1991.

Brooks, G. A., G. E. Butterfield, R. R. Wolfe, B. M. groves, R. S. Mazzeo, J. R. Sutton, E. E. Wolfel and J. T. Reeves. Decreased reliance on lactate during exercise after acclimatization to 4,300 m J. Appl. Physiol. 71:333–341, 1991

Brooks, G. A. and C. M. Donovan. Effect of training on glucose kinetics during exercise. Am. J. Physiol. 244 (Endocrinol. Metab. 7):E505–E512, 1983.

Brooks, G. A, H. Dubouchaud, M. Broun, J. P. Sicurello, and C. E. Butz. Role of mitochandrial lactic dehydrogenase and lactate oxidatiion in the 'intra-cellular lactate shuttle.' Proc. Natl. Acad. Sci. USA 96:1129–1134, 1999.

Brooks, G. A. and G. A. Gaesser. End points of lactate and glucose metabolism after exhausting exercise. J. Appl. Physiol. 49:1057–1069, 1980.

Brooks, G. A., T. D. Fahey, K. M. Baldwin, and T. P. White. EXERCISE PHYSIOLOGY: HUMAN BIOENERGETICS AND ITS APPLICATIONS, third Edition, Mayfield, Mountain view, 2000.

Brooks, G. A., E. E. Wolfel, B. M. Groves, P. R. Bender, G. E. Butterfield, A. Cymerman, R. S. Mazzeo, J. R. Sutton, R. R. Wolfe, and J. T. Reeves. Muscle accounts for glucose disposal but not lactate release during exercise after acclimatization to 4,300 m. J. Appl. Physiol. 72:2435–2445, 1992.

Brouns, F. Aspects of dehydration and rehydration in sport. Nutrition and Fitness: Metabolic and Behavioral Aspects in Health and Disease, Simopoulos, A. P. and K. N. Pavlou (eds.), Karger Publ., Basel, 1997, pp. 63–80.

Bunger, R. and R. T. Mallet. Mitochondrial pyruvate transport in working guinea pig heart. Work-related vs. carrier-mediated control of pyruvate oxidation. Biochim. biophys. Acta. 1151:223–236, 1993.

Connett, R. J., C. R. Honig, T. E. J. gayeski and G. A. Brooks. Defining hypoxia: a systems view of $VO_2$, glycolysis, energetics and intracellular $PO_2$. J. Appl. Physiol. 68:833–842, 1990.

Donovan, C. M. and G. A. Brooks. Endurance training affects lactate cleerence, not lactate production. Am. J. Physiol. 244 (Endocrinol. Metab. 7): E83–E92, 1983.

Dubouchaud, H., G. E. Butterfield, E. E. Wolfel, B. C. Bergman, and G. A. Brooks. Effect of endurance training on expression of lactate and other transport proteins in human skeletal muscle. Am. J. Physiol. Endocrinol. Metab.: 278: E571–E579, 2000.

Foster, D. W. From glycogen to ketones—and back. Diabetes 33:1188–1199, 1984.

Gaesser, G. A. and G. A. Brooks. Glycogen depletion following continuous and intermittent exercise to exhaustion. J. Appl. Physiol. 49:722–728, 1980.

Garcia, C. K., J. L. Godstein, R. K. Pathak, R. G. Anderson, and M. S. Brown. Molecular characterization of a membrane transporter for lactate, pyruvate, and other moncarboxylates: implications for the Cori cycle. Cell. 76:865–73, 1994.

Gertz, E. W., J. A. Wisneski, W. C. Stanley, and R. A. Neese. Myocardial substrate utilization during exercise in humans: dual carbon-labeled carbohydrate isotope experiments. J. Clin. Invest. 82:2017–2025, 1988.

Gladden, L. B. Net lactate uptake during progressive steady-level contractions in canine skeletal muscle. J. Appl. Physiol. 71:514–520, 1991.

Gladden, L. B., R. E. Crawford, and M. J. Webster. Effect of lactate concentration and metabolic rate on net lactate uptake by canine skeletal muscle. Am. J. Physiol. 266:R1095–101, 1994.

Halestrap, A. P. The mitochondrial pyruvate carrier. Kinetics and specificity for substrates and inhibitors. Biochem. J. 148:85–96, 1975.

Jackson, V. N., N. T. Price, L. carpenter and A. P. Halestrap. Cloning of the monocarboxylate transporter isoform MCT2 form rat testis provides evidence that expression in tissues is species-specific and may involve post-transcriptional regulation. Biochem. J. 324(Pt 2):447–453, 1997.

Kirkwood, S. P., E. A. Munn, L. Packer and G. A. Brooks. Mitochondrial reticulum in limb skeletal muscle. Am. J. Physiol. 251: C395–C402, 1986.

Kirchner, G., M. P. Scollarm, and A. M. Klibanov. Resolution of racemic mixtures via lipase catalysis in organic solvents. J. Am. Chem. Soc. 107: 7072–7076, 1985.

Kline, J. A., L. R. Thornton, G. D. Lopaschuk, R. W. Barbee, and J. A. Watts. Lactate improves cardiac efficiency after hemorrhagic shock. Shock 14: 215–221, 2000.

Mazzeo, R. S., G. A. Brooks, D. A. Schoeller and T. F. Budinger. Disposal of [$1\text{-}^{13}C$]-lactate during rest and exercise. J. Appl. Physiol. 60:232–241, 1986.

Mentzer, J. et al. Effect of pyruvate on regional ventricular function in normal and stunned myocardium. Ann. Surg. 209: (5), May, 1990.

Miller, J. M., E. F. Coyle, W. M. Sherman, J. M. Hagberg, D. L. Costill, W. J. Fink, S. E. Terblanche, and J. O. Holloszy. Effect of glycerol feeding on endurance and metabolism during prolonged exercise in man. Med. Sci. Sports Exerc. 15: 237–42, 1983.

Moleé, P. A., P. A. VanHandel and W. R. Sandel. $O_2$ consumption attributable to NADH2 during maximum lactate oxidation in the heart. *Biochem. Biophys. Resh. Comm.* 85:1143–1149, 1978.

Newgard, C. B., L. J. Hirsch, D. W. Foster and J. D. McGarry. Studies on the mechanism by which exogenous glucose is converted into liver glycogen in the rat. A direct or indirect pathway. *J. Biol. Chem.* 258:1254–1256, 1983.

Pellerin, L., G. Pellegri, P. G. Bittar, Y. Charnay, C. Bouras, J. L. Martin, N. Stella, and P. J. Magistretti. Evidence supporting the existence of an activity-dependent astrocyte-neuron lactate shuttle. *Dev. Neurosci.* 20:291–299, 1998.

Price, N. T., V. N. Jackson, and A. P. Halestrap. Cloning and sequencing of four new mammalian monocarboxylate transporter (MCT) homologues confirms the existence of a transporter family with an ancient past. *Biochem. J.*, 329:321–328, 1998.

Richter, E. A., B. Kiens, B. Saltin, N. J. Christensen and G. Savard. Skeletal muscle glucose uptake during dynamic exercise in humans: role of muscle mass. *Am. J. Physiol.* 254:E555–E561, 1988.

Roth, D. A., and G. A. Brooks, Lactate transport is mediated by a membrane-borne carrier in rat skeletal muscle sarcolemmal vesicles. *Arch. Biochem. Biophys.* 279:377–385, 1990.

Roth, D. A., and G. A. Brooks. Lactate and pyruvate transport is dominated using a pH gradient-sensitive carrier in rat skeletal muscle sarcolemmal vesicles. *Arch. Biochem. Biophys.* 279:386–394, 1990.

Stanley, W. C., E. W. Gertz, J. A. Wisneski, D. L. Morris, R. Neese and G. A. Brooks. Systemic lactate turnover during graded exercise in man. *Am. J. Physiol.* (Endocrinol. Metab. 12):249:E595–E602, 1985.

Stanlye, W. C., E. W. Gertz, J. A. Wisneski, D. L. Morris, R. Neese and G. A. Brooks. Lactate metabolism in exercising human skeletal muscle: Evidence for lactate extractin during net lactate release. *J. Appl. Physiol.* 60:1116–1120, 1986.

Stanley, W. C., J. A. Wisneski, E. W. Gertz, R. A. Neese and G. A. Brooks, Glucose and lactate interrelations during moderate intensity exercise in man. *Metabolism* 37:850–858, 1988.

Sumegi, B., B. Podanyi, P. Forgo and K. E. Kover. Metabolism of [3-$^{13}$C]pyruvate and [3-$^{13}$C]propionate in normal and ischaemic rat heart in vivo: $^1$H- and $^{13}$C-NMR studies. *Biochem. J.* 312: 75–81, 1995.

Torres, C. C. Otero. Part I. Enzymatic synthesis of lactate and glycolate esters of fatty alcohols. *Enzyme and Microbial technology.* 25: 745–752, 1999.

Trimmer, J. K., G. A. Casazza, M. A. Horning, and G. A. Brooks. Autoregulation of glucoe production in men with a glycerol load during rest and exercise. *Am. J. Physiol. Endorinol Metab* 280: E657–E668, 2001.

Wikman-Coffelt, A. et al. Alcohol and Pyruvate Cardioplegia. *J. Thorac Cardiovasc. Sug.* 101-509-16, 1991.

Wisneski, J. A., E. W. Gertz, R. A. Neese, and M. Mayr. Myocardial metabolism of free fatty acids. Studies with $^{14}$C-labeled substrates in humans. *J. Clin. Invest.* 79:359–366, 1987.

Zinker, B. A., K. Namdaran, R. Wilson, D. B. Lacy, and D. H. Wasserman. Acute adaptation of carbohydrate metabolism to decreased arterial POP2. *Am. J. Physiol.* 266:E921–929, 1994.

What is claimed is:

1. A solution comprising:

water and about 2–8% ingredients weight by volume;

wherein the ingredients comprise:

about 0.2–0.4% weight by volume of one or more acetate or lactate salts or both;

about 0.1–2% weight by volume monosaccharide or disaccharide or both;

about 2% glucose polymer; and about 0.7–7% weight by volume of one or more glycerol-ester compounds, each having the formula:

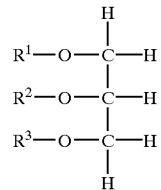

wherein R1 is an acetyl or lactoyl group, R2 is an acetyl or lactoyl group and R3 is an acetyl or lactoyl group.

2. The solution of claim 1 wherein the glucose polymer is multi-dextran.

3. The solution of claim 1 wherein the monosaccharide is fructose or glucose or both.

4. The solution of claim 1 wherein at least one of the acetate or lactate salts is a sodium salt.

5. The solution of claim 1 wherein the ingredients comprise:

about 0.2–0.4% weight by volume sodium acetate or sodium lactate or both:

about 0.1–2% weight by volume monosaccharide or disaccharide or both;

about 2% glucose polymer; and about 0.7–7% weight by volume glycerol tri-acetate ester or glycerol-tri-lactate ester or both.

6. The solution of claim 1 wherein the solution is one or more of the following:

an oral carbohydrate replacement solution, an oral water replacement solution, or an oral electrolyte replacement solution.

7. The solution of claim 1 the acetate or lactate salts are sodium salts.

8. The solution of claim 1 wherein the acetate or lactate salts comprise sodium salts.

9. The solution of claim 1 wherein the acetate or lactate salts are potassium salts.

10. The solution of claim 1 wherein the acetate or lactate salts comprise potassium salts.

11. The solution of claim 1 wherein the acetate or lactate salts are sodium salts and potassium salts.

12. The solution of claim 1, wherein the acetate or lactate salts cations comprise at least one of the following: sodium, potassium, magnesium, calcium or ammonium.

13. The solution of claim 1 wherein the one or more compounds comprise glycerol-triacetate ester and glycerol-trilactate ester.

14. The solution of claim 1 wherein the one or more compounds comprises glycerol-triacetate ester.

15. The solutin of claim 1 wherein the one or more compounds comprises glycerol-trilactate ester.

16. A solution comprising:

water and two or more glycerol-ester compounds, each having the formula:

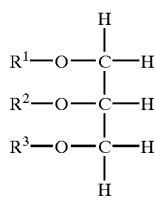

wherein R1 is an acetyl or lactoyl group, R2 is an acetyl or lactoyl group and R3 is an acetyl or lactoyl group;

wherein one of the glycerol-ester compounds comprises about 10–90% of the total glycerol-ester compounds by weight, and the one of the glycerol-ester compounds is glycerol-triacetate ester or glycerol-trilactate ester.

17. The solution of claim 16 wherein the solution further comprises a glucose polymer.

18. The solution of claim 16 wherein the solution further comprises a monosaccharide.

19. The solution of claim 16 wherein the solution further comprises acetate or lactate salts or both.

20. A method of replacing one or more of the following lost due to exercise: carbohydrates, water and electrolytes, the method comprising administering the following solution orally:

water and about 2–8% ingredients weight by volume;
wherein the ingredients comprise:
about 0.2–0.4% weight by volume of one or more acetate or lactate salts or both;
about 0.1–2% weight by volume monosaccharide or disaccharide or both;
about 2% glucose polymer; and
about 0.7–7% weight by volume of one or more glycerol-ester compounds, each having the formula:

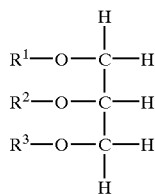

wherein R1 is an acetyl or lactoyl group, R2 is an acetyl or lactoyl group and R3 is an acetyl or lactoyl group.

21. A method of replacing one or more of the following lost due to exercise: carbohydrates, water and electrolytes, the method comprising:

oral administration of a solution comprising:
water and two or more glycerol-ester compounds, each having the formula:

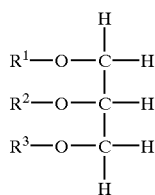

wherein R1 is an acetyl or lactoyl group, R2 is an acetyl or lactoyl group and R3 is an acetyl or lactoyl group;

wherein one of the glycerol-ester compounds comprises about 10–90% of the total glycerol-ester compounds by weight, and the one of the glycerol-ester compounds is glycerol-triacetate ester or glycerol-trilactate ester.

22. A method of replacing one or more of the following lost due to exercise: carbohydrates, water and electrolytes, the method comprising:

oral administration of a solution comprising:
water and one or more glycerol-ester compounds, each having the formula:

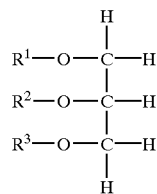

wherein R1 is an acetyl or lactoyl group, R2 is an acetyl or lactoyl group and R3 is an acetyl or lactoyl group.

23. The method of claim 22 wherein the one or more compounds comprises glycerol-triacetate ester.

24. The method of claim 22 wherein the one or more compounds comprises glycerol-trilactate ester.

25. The method of claim 22 wherein the one or more compounds is about 0.7–7% weight by volume.

26. The method of claim 22 wherein the solution further comprises a glucose polymer.

27. The method of claim 22 wherein the solution further comprises a monosaccharide.

28. The method of claim 22 wherein the solution further comprises acetate or lactate salts or both.

29. The method of claim 28 wherein the acetate or lactate salts comprise sodium salts.

30. The method of claim 28 wherein the acetate or lactate salts comprise potassium salts.

31. The method of claim 28 wherein the acetate or lactate salts cations comprise at least one of the following: sodium, potassium, magnesium, calcium or ammonium.

32. A solution, comprising:

water and two or more glycerol-ester compounds, each having the formula:

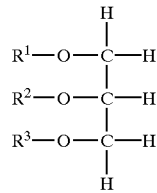

wherein R1 is an acetyl or lactoyl group, R2 is an acetyl or lactoyl group and R3 is an acetyl or lactoyl group;

wherein one of the glycerol-ester compounds comprises about 10–90% of the total glycerol-ester compounds by weight, and the one of the glycerol-ester compounds is glycerol-triacetate ester or glycerol-trilactate ester;

wherein the two or more glycerol-ester compounds are synthesized by:
placing glycerol, an organic solvent, and acetic acid or L-lactic acid or both, in a container; and
adding lipase.

33. The solution of claim 32 wherein the solution further comprises:

water and about 2–8% ingredients weight by volume;
wherein the ingredients comprise:
- about 0.2–0.4% weight by volume of one or more acetate or lactate salts or both;
- about 0.1–2% weight by volume monosaccharide or disaccharide or both;
- about 2% glucose polymer; and
- about 0.7–7% weight by volume of two or more glycerol-ester compounds.

34. The solution of claim 32 wherein the lipase is from *Candida Antarctica*.

35. The solution of claim 32 wherein the two or more glycerol-ester compounds are further synthesized by:

placing in a container lipase B from *Candida Antarctica*, about 25 parts L-lactic acid at about 0.55 mmol, about 25 parts glycerol at about 0.55 mmol, out 1 part acetone or acetonitrile, about $1.4 \times 10^{-4}$ $\mu$ Activities lipase B per part 25 parts of L-lactic acid;

and reacting the mixture for about 24 hours at about 50° C.

* * * * *